US008518986B2

(12) United States Patent
Oddos et al.

(10) Patent No.: US 8,518,986 B2
(45) Date of Patent: Aug. 27, 2013

(54) COMPOSITIONS CONTAINING RETINOID AND CHROMENONE DERIVATIVES

(75) Inventors: Thierry Oddos, Menden (FR); Otto Von Stetten, Aachen (DE); Anne-Sophie Brillouet, Los Angeles, CA (US); Nathalie Issachar, Paris (FR)

(73) Assignee: Johnson & Johnson Consumer France, S.A.S. (FR)

( * ) Notice: Subject to any disclaimer, the term of this patent is extended or adjusted under 35 U.S.C. 154(b) by 760 days.

(21) Appl. No.: 12/115,734

(22) Filed: May 6, 2008

(65) Prior Publication Data

US 2009/0281173 A1 Nov. 12, 2009

(51) Int. Cl.
*A01N 43/16* (2006.01)
*A61K 31/35* (2006.01)
*A61K 8/02* (2006.01)

(52) U.S. Cl.
USPC .......................................... 514/456; 424/401

(58) Field of Classification Search
None
See application file for complete search history.

(56) References Cited

U.S. PATENT DOCUMENTS 5,589,178 A * 12/1996 Aubert et al. ................ 424/401
2004/0067246 A1* 4/2004 Msika et al. ................. 424/401
2005/0043398 A1 2/2005 Carola
2007/0141014 A1* 6/2007 Pflucker et al. ........... 424/70.31

FOREIGN PATENT DOCUMENTS

WO WO 2007087956 A1 * 8/2007

OTHER PUBLICATIONS

Lee et al., A newly synthesized photostable retinol derivative (retinyl N-formyl aspartmate) for photodamaged skin: Profilometric evaluation of 24-week study, Journal of the American Academy of Dermatology, C.V. Mosby, St. Louis, MD, US, vol. 55, No. 2, Aug. 2006, pp. 220-224, XP005540616 ISSN: 0190-9622, p. 220.
EPO Search Report dated Jun. 21, 2007.

* cited by examiner

*Primary Examiner* — Fereydoun G Sajjadi
*Assistant Examiner* — Michael B Pallay

(57) ABSTRACT

The present invention relates to a composition including at least one retinoid and at least one chromenone derivative and the use thereof for the preparation of a cosmetic article to be used for the topical application to skin, hair or nails.

2 Claims, No Drawings

COMPOSITIONS CONTAINING RETINOID AND CHROMENONE DERIVATIVES

BACKGROUND OF THE INVENTION

The human skin is subject to certain aging processes, some of which are attributable to intrinsic processes (e.g., chrono-aging) and some of which are attributable to exogenous factors (e.g., photo-aging). In addition, temporary or even lasting changes to the skin can occur, such as acne, greasy or dry skin, keratoses, rosacea, light-sensitive, inflammatory, erythematous, and allergic or autoimmune-reactive reactions, such as dermatosis and photodermatosis.

The consequences of the above-mentioned aging processes can include thinning of the skin, weaker interlacing of epidermis and dermis, and a reduction in the number of cells and the supplying blood vessels. This often results in the formation of fine lines and wrinkles, and pigment defects can occur.

Retinoids, such as retinoic acid, retinol and esters thereof, and tazorotene, act on the differentiation of epithelial cells and are therefore employed for the prophylaxis and treatment of numerous phenomena which impair the skin state. For example use against acne, psoriasis, senile keratosis, skin discoloration and wrinkles has been described. See, e.g., PCT Patent Applications Nos. WO 93/19743 and WO 02/02074.

Certain chromenone derivatives have been shown to exhibit certain anti-aging effects. See US Patent Application 2005/0043398. However, such chromenone derivatives were suggested not to be combined with retinoids (US Patent Application 20050043398, paragraph 63). Applicants have surprisingly found that such chromenone derivatives actually effectively potentiate the topical efficacy of retinoids.

SUMMARY OF THE INVENTION

The present invention relates to a composition including at least one retinoid and at least one chromenone derivative and the use thereof for the preparation of an article to be used for the topical application to skin, hair or nails.

Other features and advantages of the present invention will be apparent from the detailed description of the invention and from the claims.

DETAILED DESCRIPTION OF THE INVENTION

It is believed that one skilled in the art can, based upon the description herein, utilize the present invention to its fullest extent. The following specific embodiments can be construed as merely illustrative, and not limitative of the remainder of the disclosure in any way whatsoever.

Unless defined otherwise, all technical and scientific terms used herein have the same meaning as commonly understood by one of ordinary skill in the art to which the invention belongs. Also, all publications, patent applications, patents, and other references mentioned herein are incorporated by reference. As used herein, all percentages are by weight unless otherwise specified.

DEFINITIONS

As used herein, “topical application” and “topically applying” means directly laying on or spreading on the skin, hair, or nail, e.g., by use of the hands or an applicator such as a wipe.

As used herein, “cosmetically-acceptable” means that cosmetically active agents, inert ingredients, or composition which the term describes are suitable for use (e.g., as a cosmetic or pharmaceutical) in contact with tissues (e.g., the skin) without undue toxicity, incompatibility, instability, irritation, allergic response, and the like, commensurate with a reasonable benefit/risk ratio.

Retinoids

The compositions of the present invention contain one or more retinoids. Examples of retinoids include, but are not limited to, retinol, retinoic acid, retinal, and salts and esters thereof, such as retinyl palmitate, retinyl propionate, and retinyl acetate. In one embodiment, the composition contains retinol, such as all-trans-retinol. Other retinoids are disclosed in U.S. Pat. No. 5,051,449. Of course, also mixtures of two, three or more retinoids can be used with the compositions of the present invention.

In one embodiment, the composition includes a cosmetically-acceptable amount of the retinoid. The retinoid typically will be present in the composition in an amount from about 0.001% to about 5% by weight, in particular in an amount from about 0.005% to about 2% by weight, such as from about 0.01% to about 0.5%.

Chromenone Derivative

The compositions of the present invention contain one, two, three or more chromenone derivatives of Formula I (Formula I)

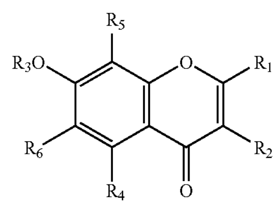

or salt thereof where:

$R^1$ and $R^2$ are identical or different, and are selected from the group consisting of H, —C(═O)—$R^7$, —C(═O)—$OR^7$, a straight-chain or branched $C_1$- to $C_{20}$-alkyl group, wherein the alkyl is optionally at least once interrupted by oxygen, a straight-chain or branched $C_3$- to $C_{20}$-alkenyl group, a straight-chain or branched $C_1$- to $C_{20}$-hydroxyalkyl group, where the hydroxyl group is bonded to a primary or secondary carbon atom of the alkyl, and wherein the alkyl is optionally at least once interrupted by oxygen, and a $C_3$- to $C_{10}$-cycloalkyl group or a $C_3$- to $C_{12}$-cycloalkenyl group (where the cyclic group is optionally bridged by —$(CH_2)_n$— group where n=1 to 3);

$R^3$ is H or a straight-chain or branched $C_1$- to $C_{20}$-alkyl group;

$R^4$ is H or —$OR^8$;

$R^5$ and $R^6$ are identical or different, and are selected from the group consisting of H or —OH, a straight-chain or branched $C_1$- to $C_{20}$-alkyl group (wherein the alkyl is optionally at least once interrupted by oxygen), a straight-chain or branched $C_3$- to $C_{20}$-alkenyl group, and a straight-chain or branched $C_1$- to $C_{20}$-hydroxyalkyl group (where the hydroxyl group is bonded to a primary or secondary carbon atom of the alkyl and wherein the alkyl is optionally at least once interrupted by oxygen);

$R^7$ is H, a straight-chain or branched $C_1$- to $C_{20}$-alkyl group; and $R^8$ is H or a straight-chain or branched $C_1$- to $C_{20}$-alkyl group.

In one embodiment at least two of the substituents $R^1$, $R^2$, $R^4$, $R^5$, and $R^6$ are different from H or at least one substituent from $R^1$ and $R^2$ is —C(═O)—$R^7$ or —C(═O)—$OR^7$.

In one embodiment, $R^1$ is selected from the group consisting of H, —C(═O)—$R^7$, —C(═O)—$OR^7$, a straight or branched $C_1$- to $C_8$-alkyl group, such as methyl, ethyl, i-propyl, n-propyl, n-butyl, i-butyl, t-butyl, pentyl, hexyl, heptyl, or octyl, including all isomeric forms, e.g. 3-heptyl or 3-octyl, (wherein the alkyl is optionally at least once interrupted by oxygen, such as methylene methoxide); $R^2$ is selected from the group consisting of H, —C(═O)—$R^7$, or —C(═O)—$OR^7$; $R^3$ is selected from the group consisting of H or a straight-chain or branched $C_1$- to $C_8$-alkyl group, such as methyl, ethyl, i-propyl, n-propyl, n-butyl, i-butyl, t-butyl, pentyl, hexyl, heptyl, or octyl, including all isomeric forms, e.g. 3-heptyl or 3-octyl; $R^4$ is selected from the group consisting of H or OH; $R^5$ is selected from the group consisting of H, OH and $C_3$- to $C_{10}$-alkenyl, e.g. $C_4$- or $C_5$-alkenyl, such as 3-methyl-but-2-en; $R^6$ is selected from the group consisting of H, OH and $C_3$- to $C_{10}$-alkenyl, e.g. $C_4$- or $C_5$-alkenyl, such as 3-methyl-but-2-en; and $R^7$ is selected from the group consisting of H, a straight-chain or branched $C_1$- to $C_8$-alkyl group, such as methyl, ethyl, i-propyl, n-propyl, n-butyl, i-butyl, t-butyl, pentyl, hexyl, heptyl, or octyl, including all isomeric forms, e.g. 3-heptyl or 3-octyl, wherein the alkyl is optionally at least once interrupted by oxygen, such as methylene methoxide, and a di- or polyhydroxyl radical such as a straight-chain or branched $C_1$- to $C_8$-di- or polyhydroxyl alkyl group.

Particular preferred compounds are selected from the compounds of the formula I such as

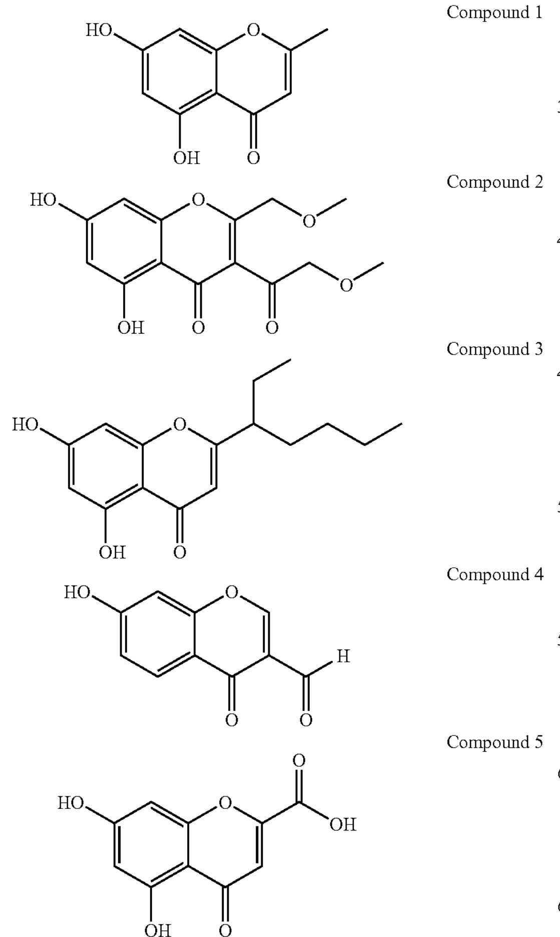

-continued

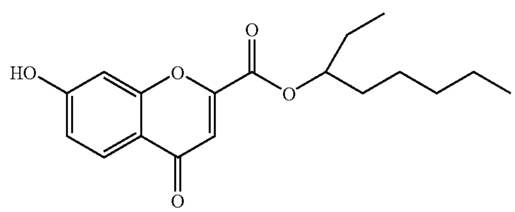

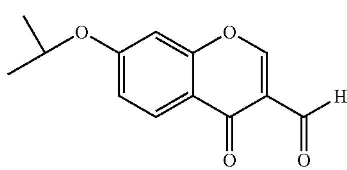

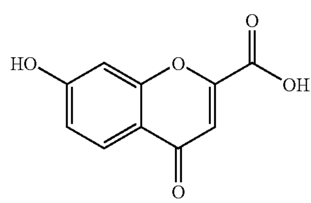

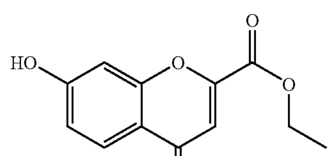

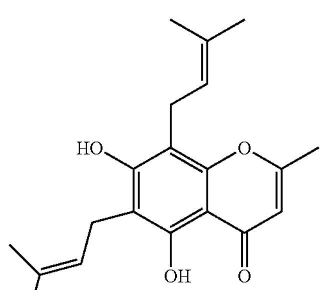

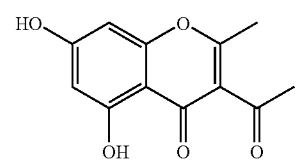

The compounds of the present invention such as the retinoids and/or the chromenone derivatives may also be present in the form of cosmetically-acceptable salts. For use in medicine, the salts of the compounds of this invention refer to non-toxic "cosmetically-acceptable salts," cosmetically-acceptable acidic/anionic or basic/cationic salts. Cosmetically-acceptable acidic/anionic salts include, and are not limited to acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, nitrate, pamoate, pantothenate, phosphate/diphospate, polygalacturonate, salicylate, stearate, subacetate, succinate, sulfate, tannate, tartrate, teoclate, tosylate and triethiodide. Cosmetically-acceptable basic/cationic salts include, and are not limited to aluminum, benzathine, calcium, chloroprocaine, choline, diethanolamine, ethylenediamine, lithium, magnesium, meglumine, potassium, procaine, sodium and zinc. Other salts may, however, be useful in the preparation of compounds according to this invention or of their cosmetically-acceptable salts. Organic or inorganic acids also include, and are not limited to, hydriodic, perchloric, sulfuric, phosphoric, propionic, glycolic, methanesulfonic, hydroxyethanesulfonic, oxalic, 2-naphthalenesulfonic, p-toluenesulfonic, cyclohexanesulfamic, saccharinic or trifluoroacetic acid.

The chromenone derivatives of the present invention can be synthesized by one of ordinary skill in the art. Examples of such synthesis are disclosed in U.S. Patent Application 2005/0043398, which is incorporated herein by reference.

In one embodiment, the composition includes a cosmetically-acceptable amount of the chromenone derivative. In one embodiment the chromenone derivative(s) can be present in the composition in an amount from about 0.001% to about 5% by weight, in particular in an amount from about 0.01% to about 2% by weight, such as from about 0.05% to about 0.5%.

Compositions

The composition and products containing such compositions of the present invention may be prepared using methodology that is well known by an artisan of ordinary skill.

The compositions useful in the present invention involve formulations suitable for administering to the target tissues, such as mammalian skin such as human skin. In one embodiment, the composition contains a cosmetically-acceptable amount of (i) a retinoid, such as retinol, (ii) a chromenone derivatives, such as Compound 1, and (iii) a cosmetically-acceptable carrier, such as an emulsion.

The compositions may be made into a wide variety of articles that include but are not limited to lotions, creams, gels, sticks, sprays, ointments, cleansing liquid washes and solid bars, shampoos and hair conditioners, pastes, foams, powders, mousses, shaving creams, wipes, strips, patches, electrically-powered patches, wound dressing and adhesive bandages, hydrogels, film-forming products, facial and skin masks, make-up such as foundations, eye liners, and eye shadows, and the like. These product types may contain several types of cosmetically-acceptable carriers including, but not limited to solutions, suspensions, emulsions such as microemulsions and nanoemulsions, gels, solids and liposomes. Such articles may be distributed as a pharmaceutical, an over-the-counter medication, or cosmetic. The following are non-limitative examples of such carriers. Other carriers can be formulated by those of ordinary skill in the art.

The compositions useful in the present invention can be formulated as solutions. Solutions typically include an aqueous or organic solvent (e.g., from about 50% to about 99.99% or from about 90% to about 99% of a cosmetically-acceptable aqueous or organic solvent). Examples of suitable organic solvents include but are not limited to propylene glycol, polyethylene glycol (e.g. 200-600), polypropylene glycol (e.g. 425-2025), glycerol, 1,2,4-butanetriol, sorbitol esters, 1,2,6-hexanetriol, ethanol, and mixtures thereof.

A lotion can be made from such a solution. Lotions typically contain from about 1% to about 20% (e.g., from about 5% to about 10%) of an emollient(s) and from about 50% to about 90% (e.g., from about 60% to about 80%) of water. As used herein, "emollients" refer to materials used for the prevention or relief of dryness, as well as for the protection of the skin or hair. Examples of emollients include, but are not limited to, those set forth in the International Cosmetic Ingredient Dictionary and Handbook, eds. Wenninger and McEwen, pp. 1656-61, 1626, and 1654-55 (The Cosmetic, Toiletry, and Fragrance Assoc., Washington, D.C., $7^{th}$ Edition, 1997) (hereinafter "ICI Handbook").

Another type of product that may be formulated from a solution is a cream. A cream typically contains from about 5% to about 50% (e.g., from about 10% to about 20%) of an emollient(s) and from about 45% to about 85% (e.g., from about 50% to about 75%) of water.

Yet another type of product that may be formulated from a solution is an ointment. An ointment may contain a simple base of animal, vegetable, or synthetic oils or semi-solid hydrocarbons. An ointment may contain from about 2% to about 10% of an emollient(s) plus from about 0.1% to about 2% of a thickening agent(s). Examples of thickening agents include, but are not limited to, those set forth in the ICI Handbook pp. 1693-1697.

The compositions useful in the present invention can also be formulated as emulsions. If the carrier is an emulsion, from about 1% to about 10% (e.g., from about 2% to about 5%) of the carrier contains an emulsifier(s). Emulsifiers may be nonionic, anionic, cationic, or zwitterionic. Examples of emulsifiers include, but are not limited to, those set forth in the ICI Handbook, pp. 1673-1686.

Lotions and creams can be formulated as emulsions. Typically such lotions contain from 0.5% to about 5% of an emulsifier(s), while such creams would typically contain from about 1% to about 20% (e.g., from about 5% to about 10%) of an emollient(s); from about 20% to about 80% (e.g., from 30% to about 70%) of water; and from about 1% to about 10% (e.g., from about 2% to about 5%) of an emulsifier(s).

Single emulsion skin care preparations, such as lotions and creams, of the oil-in-water type and water-in-oil type are well-known in the art and are useful in the subject invention, including but not limited to silicone-in-water and water-in-silicone emulsions. Multiphase emulsion compositions, such as the water-in-oil-in-water type or the oil-in-water-in-oil type, are also useful in the subject invention. In general, such single or multiphase emulsions contain water, emollients, and emulsifiers as essential ingredients.

The compositions of this invention can also be formulated as a gel (e.g., an aqueous, alcohol, alcohol/water, or oil gel using a suitable gelling agent(s)). Suitable gelling agents for aqueous and/or alcoholic gels include, but are not limited to, natural gums, acrylic acid and acrylate polymers and copolymers, and cellulose derivatives (e.g., hydroxymethyl cellulose and hydroxypropyl cellulose). Suitable gelling agents for oils (such as mineral oil) include, but are not limited to, hydrogenated butylene/ethylene/styrene copolymer and hydrogenated ethylene/propylene/styrene copolymer. Such gels typically contain between about 0.1% and 5%, by weight, of such gelling agents.

The compositions of the present invention can also be formulated into a solid formulation (e.g., a wax-based stick, soap bar composition, powder, and wipe containing powder).

The composition of the present invention can also be formulated as a suspension, including but not limited to, a solid lipid nanonized particle suspension.

The compositions useful in the subject invention may contain, in addition to the aforementioned components, a wide variety of additional oil-soluble materials and/or water-soluble materials conventionally used in compositions for use on skin at their art-established levels.

Additional Cosmetically Active Agents

In one embodiment, the topical composition further includes additional cosmetically active agent. What is meant by a "cosmetically active agent" is a compound that has a cosmetic or therapeutic effect on the skin, hair, or nails, e.g., lightening agents, darkening agents such as self-tanning agents, anti-acne agents, shine control agents, anti-microbial agents, anti-inflammatory agents, anti-mycotic agents, anti-parasite agents, external analgesics, sunscreens, photoprotectors, antioxidants, keratolytic agents, detergents/surfactants, moisturizers, nutrients, vitamins, energy enhancers, anti-perspiration agents, astringents, deodorants, hair removers, firming agents, anti-callous agents, and agents for hair, nail, and/or skin conditioning. Cosmetically-active agents include pharmaceutical active agents.

In one embodiment, the cosmetically active agent is selected from, but not limited to, the group consisting of hydroxy acids, benzoyl peroxide, sulfur resorcinol, caffeine, ascorbic acid, D-panthenol, hydroquinone, octyl methoxycinnimate, titanium dioxide, octyl salicylate, homosalate, avobenzone, polyphenolics, carotenoids, free radical scavengers, ceramides, polyunsaturated fatty acids, essential fatty acids, enzymes, enzyme inhibitors, minerals, hormones such as estrogens, steroids such as hydrocortisone, 2-dimethylaminoethanol, copper salts such as copper chloride, coenzyme Q10, lipoic acid, amino acids such a proline and tyrosine, vitamins, lactobionic acid, acetyl-coenzyme A, niacin, riboflavin, thiamin, ribose, electron transporters such as NADH and FADH2, and other botanical extracts such as aloe vera, feverfew, soy, climbing ivy (*Hedera helix*), arnica (*Arnica Montana*), rosemary (*Rosmarinus officinalis* N), sage (*Salvia officinalis* N), ginseng (*Panax ginseng*), St. Johns-wart (*Hypericum perforatum*), ruscus (*Ruscus aculatus*), meadowsweet (*Filipendula ulmaria* L), and orthosiphon (*Ortosifon stamincus* Benth), Forskolin, and derivatives and mixtures thereof. The cosmetically-active agent will typically be present in the composition of the invention in an amount of from about 0.001% to about 20% by weight of the composition, e.g., about 0.01% to about 10% such as about 0.1% to about 5%.

Examples of vitamins include, but are not limited to, vitamin Bs (such as vitamin B3, vitamin B5, and vitamin B12), vitamin C, vitamin K, and vitamin E, and derivatives thereof.

In one embodiment, the composition also contains an antioxidant. Examples of antioxidants include, but are not limited to, water-soluble antioxidants such as sulfhydryl compounds and their derivatives (e.g., sodium metabisulfite and N-acetyl-cysteine), lipoic acid and dihydrolipoic acid, resveratrol, lactoferrin, ascorbic acid, and ascorbic acid derivatives (e.g., ascorbyl palmitate and ascorbyl polypeptide). Oil-soluble antioxidants suitable for use in the compositions of this invention include, but are not limited to, butylated hydroxytoluene, tocopherols (e.g., tocopheryl acetate), tocotrienols, and ubiquinone. Natural extracts containing antioxidants suitable for use in the compositions of this invention, include, but not limited to, extracts containing flavonoids and isoflavonoids and their derivatives (e.g., genistein and diadzein), extracts containing resveratrol and the like. Examples of such natural extracts include grape seed, green tea, pine bark, and propolis. Other examples of antioxidants may be found on pages 1612-13 of the ICI Handbook.

Other Materials

Various other cosmetically-active agents may also be present in the skin care products. These include, but are not limited to, skin protectants, humectants, and emollients. The composition may also include chelating agents (e.g., EDTA), preservatives (e.g., parabens), pigments, dyes, opacifiers (e.g., titanium dioxide), and fragrances.

The composition and products containing such compositions of the present invention may be prepared using methodology that is well known by an artisan of ordinary skill.

Uses

The composition according to the invention can be used to treat a variety of hair, nail and skin conditions, such as (i) reducing the appearance of the signs of aging (e.g., reducing the appearance of wrinkles and fine lines), cellulite, stretch-marks, light or dark areas, pores, and oil on the skin and (ii) treating dry skin and acne, and (iii) enhancing the firmness and/or elasticity of the skin.

Example 1

Topical Compositions

The four topical compositions set forth in Table 1 were manufactured as follows.

First, the C10-30 Alkyl acrylates crosspolymer and Disodium EDTA were added to the water, and the mixture was allowed to thicken for 15 min. The mixture was then heated to 75° C., and the sodium hydroxide mixture was added to form Phase A. Then, the methylparaben, propylparaben, and Phenoxyethanol were mixed together and added to Phase A.

The glyceryl stearate (and) PEG-stearate, isononyl isononanoate, cetyl alcohol, and BHT were mixed together and heated to 85° C. to for Phase B. Phase B was then added to Phase A, and the resulting mixture was cooled. The ethanol, PEG-8, and butylene glycol (with or without Compound 1) were added to the cooled mixture. Finally, the ascorbic acid and optionally retinol were added to the cooled mixture.

TABLE I

| INCI NAME | COMPOUND 1 (0.1%) | Retinol (0.04%) and COMPOUND 1 (0.1%) | Retinol (0.04%) | Retinol (0.1%) |
|---|---|---|---|---|
| Water | q.s. 100 | q.s. 100 | q.s. 100 | q.s. 100 |
| C10-30 Alkyl acrylates crosspolymer | 0.4 | 0.4 | 0.4 | 0.4 |
| Disodium EDTA | 0.1 | 0.1 | 0.1 | 0.1 |
| Methylparaben | 0.2 | 0.2 | 0.2 | 0.2 |
| Propylparaben | 0.15 | 0.15 | 0.15 | 0.15 |
| Phenoxyethanol | 0.50 | 0.50 | 0.50 | 0.50 |
| Sodium Hydroxide 10%/Water 90% | 1 | 1 | 1 | 1 |
| Glyceryl stearate (and) PEG-stearate | 2 | 2 | 2 | 2 |
| BHT | 0.1 | 0.1 | 0.1 | 0.1 |
| Cetyl alcohol | 1 | 1 | 1 | 1 |
| Isononyl isononanoate | 7 | 7 | 7 | 7 |
| PEG8 | 4 | 4 | 4 | 4 |
| Butylene Glycol | 4 | 4 | 4 | 4 |
| Alcohol | 4 | 4 | 4 | 4 |
| Compound 1 | 0.1 | 0.1 | — | — |
| Ascorbic Acid | 0.05 | 0.05 | 0.05 | 0.05 |
| Retinol 40%/Polysorbate 20 60% | 0 | 0.1 | 0.1 | 0.24 |

Example 2

Clinical Study

The compositions of Example 1 containing retinol, Compound 1, or a combination thereof were assessed in a double-blind, clinical study performed on 34 female volunteers between 42 and 59 years old.

Products were applied once a day on half of the face of volunteers. The study was performed in double blind conditions. Wrinkles of the under-eye area were analyzed by clinical assessment of experts at initiation of the study and after 12 weeks of application. The results obtained with each product after 12 weeks were compared with the results obtained at in initiation of the study ("Baseline").

The results (summarized in Table 2 below) show that the combination of retinol and Compound 1 were able to deliver a significant reduction in the appearance of wrinkle of the under eye area, an unexpected over seven fold improvement as compared to the same concentration of retinol alone. The combination delivered an even higher level of efficacy as the composition containing a much higher concentration of retinol, thus allowing for the reduction of retinol level in products (e.g., to reduce any retinol-induced irritation) without loss in product efficacy.

| Test Product | % Improvement vs. Baseline |
|---|---|
| Retinol 0.04% | 2 |
| Retinol 0.1% | 12* |
| Compound 1 0.1% | 0 |
| Retinol 0.04% and Compound 1 0.1% | 15* |

*Significant difference versus placebo

What is claimed is:

1. A composition comprising (i) from about 0.04 to about 2% by weight of retinol and (ii) from about 0.1 to about 2% by weight of at least one chromenone compound of Formula I (Formula I)

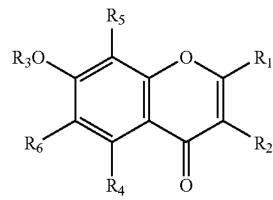

or salt thereof where:

$R^1$ and $R^2$ are identical or different, and are selected from the group consisting of H, —C(═O)—$R^7$, —C(═O)—$OR^7$, a straight-chain or branched $C_1$- to $C_{20}$-alkyl group, wherein the alkyl is optionally at least once interrupted by oxygen, a straight-chain or branched $C_3$- to $C_{20}$-alkenyl group, a straight-chain or branched $C_1$- to $C_{20}$-hydroxyalkyl or -di- or polyhydroxyalkyl group, where the hydroxyl group is bonded to a primary or secondary carbon atom of the alkyl, and wherein the alkyl is optionally at least once interrupted by oxygen, a $C_3$- to $C_{10}$-cycloalkyl group and a $C_3$- to $C_{12}$-cycloalkenyl group (where the cyclic group is optionally bridged by —$(CH_2)_n$— group where n=1 to 3);

$R^3$ is H or a straight-chain or branched $C_1$- to $C_{20}$-alkyl group;

$R^4$ is H or —$OR^8$;

$R^5$ and $R^6$ are identical or different, and are selected from the group consisting of H or —OH, a straight-chain or branched $C_1$- to $C_{20}$-alkyl group (wherein the alkyl is optionally at least once interrupted by oxygen), a straight-chain or branched $C_3$- to $C_{20}$-alkenyl group, and a straight-chain or branched $C_1$- to $C_{20}$-hydroxyalkyl group, where the hydroxyl group is bonded to a primary or secondary carbon atom of the alkyl, and wherein the alkyl is optionally at least once interrupted by oxygen;

$R^7$ is selected from the group consisting of H, a straight-chain or branched $C_1$- to $C_{20}$-alkyl group, wherein the alkyl is optionally at least once interrupted by oxygen, a straight-chain or branched $C_3$- to $C_2$O-alkenyl group, and a straight-chain or branched $C_1$- to $C_{20}$-hydroxyalkyl or -di- or polyhydroxyalkyl group, where the hydroxyl group is bonded to a primary or secondary carbon atom of the alkyl and wherein the alkyl is optionally at least once interrupted by oxygen, and $R^8$ is H or a straight-chain or branched $C_1$- to $C_{20}$-alkyl group.

2. A composition according to claim 1, wherein $R^5$ and $R^6$ are H.

* * * * *